(12) United States Patent
Nowak et al.

(10) Patent No.: US 9,861,456 B2
(45) Date of Patent: Jan. 9, 2018

(54) DEVICE FOR DETECTING THE THREE-DIMENSIONAL GEOMETRY OF OBJECTS AND METHOD FOR THE OPERATION THEREOF

(71) Applicant: a.tron3d GmbH, Klagenfurt am Wörthersee (AT)

(72) Inventors: Christoph Nowak, Vienna (AT); Horst Koinig, Klagenfurt (AT); Jurgen Jesenko, Finkenstein (AT)

(73) Assignee: A.TRON3D GMBH, Klagenfurt Am (AT)

( * ) Notice: Subject to any disclaimer, the term of this patent is extended or adjusted under 35 U.S.C. 154(b) by 230 days.

(21) Appl. No.: 14/377,030

(22) PCT Filed: Feb. 4, 2013

(86) PCT No.: PCT/AT2013/000018
§ 371 (c)(1),
(2) Date: Aug. 6, 2014

(87) PCT Pub. No.: WO2013/116881
PCT Pub. Date: Aug. 15, 2013

(65) Prior Publication Data
US 2015/0282902 A1    Oct. 8, 2015

(30) Foreign Application Priority Data
Feb. 6, 2012    (DE) .................. 10 2012 100 953

(51) Int. Cl.
*A61C 9/00*    (2006.01)
*A61B 5/107*    (2006.01)
(Continued)

(52) U.S. Cl.
CPC ............ *A61C 9/006* (2013.01); *A61B 5/1076* (2013.01); *A61B 5/1077* (2013.01);
(Continued)

(58) Field of Classification Search
CPC ... A61B 5/1076; A61B 5/1077; A61B 5/4547; A61B 2560/0209; A61C 9/006;
(Continued)

(56) References Cited

U.S. PATENT DOCUMENTS 4,837,732 A    6/1989    Brandestini et al.
5,661,519 A    8/1997    Franetzki
(Continued)

FOREIGN PATENT DOCUMENTS

AT    508 563 B    2/2011
DE    196 36 354 A1    3/1998
(Continued)

OTHER PUBLICATIONS

International Search Report, dated Jun. 20, 2013, from corresponding PCT application.

*Primary Examiner* — Nicholas Lucchesi
(74) *Attorney, Agent, or Firm* — Young & Thompson

(57) ABSTRACT

A device for detecting the three-dimensional geometry of objects (9), in particular teeth, includes a handpiece (1) which is provided with at least one position sensor (12) for detecting the change of the spatial position of the handpiece (1), and an optical device (2) having at least one camera (5, 6) for capturing images and at least one light source (3) for at least one projector (4). The position sensor (12) in the handpiece (1) initially determines the size of the change of the spatial position of the device. It is determined therefrom, how many pictures the camera (5, 6) can take in a defined time unit.

15 Claims, 2 Drawing Sheets

(51) Int. Cl.
  *G01B 21/04* (2006.01)
  *G01B 11/25* (2006.01)
  *A61B 5/00* (2006.01)
  *G01B 11/02* (2006.01)
  *G06T 7/00* (2017.01)
  *H04N 7/18* (2006.01)
  *H04N 13/00* (2006.01)
  *H04N 13/02* (2006.01)

(52) U.S. Cl.
  CPC .......... *A61B 5/1079* (2013.01); *A61B 5/4547* (2013.01); *G01B 11/022* (2013.01); *G01B 11/2513* (2013.01); *G01B 21/042* (2013.01); *G06T 7/0012* (2013.01); *H04N 7/18* (2013.01); *H04N 13/0055* (2013.01); *H04N 13/0059* (2013.01); *H04N 13/0221* (2013.01); *H04N 13/0253* (2013.01); *A61B 2560/0209* (2013.01); *H04N 2213/001* (2013.01)

(58) Field of Classification Search
  CPC  G01B 11/022; G01B 11/2513; G01B 21/042; G06T 7/0012; H04N 7/18
  USPC .................................................. 433/29, 215
  See application file for complete search history.

(56) References Cited

U.S. PATENT DOCUMENTS

| | | | |
|---|---|---|---|
| 7,522,764 B2* | 4/2009 | Schwotzer | A61B 1/24 356/601 |
| 9,101,434 B2* | 8/2015 | Nowak | A61C 9/006 |
| 2005/0090749 A1 | 4/2005 | Rubbert | |
| 2009/0087050 A1* | 4/2009 | Gandyra | G01B 11/03 382/128 |
| 2010/0021867 A1* | 1/2010 | Altshuler | A61C 1/0046 433/215 |
| 2010/0239136 A1 | 9/2010 | Gandyra et al. | |
| 2010/0284589 A1 | 11/2010 | Thiel et al. | |
| 2011/0242281 A1 | 10/2011 | Schmidt | |
| 2012/0218389 A1 | 8/2012 | Nowak et al. | |
| 2012/0235495 A1* | 9/2012 | Eggert | H02J 7/345 307/80 |
| 2012/0237889 A1* | 9/2012 | Nowak | G01B 11/2513 433/29 |
| 2013/0034825 A1* | 2/2013 | Phillips | A61B 1/00016 433/29 |
| 2013/0286174 A1* | 10/2013 | Urakabe | A61B 1/00009 348/66 |
| 2014/0071258 A1 | 3/2014 | Gandyra | |
| 2014/0104406 A1* | 4/2014 | Pfeiffer | G01B 11/2441 348/77 |
| 2014/0272774 A1* | 9/2014 | Dillon | A61C 9/0053 433/29 |
| 2014/0272775 A1* | 9/2014 | Monty | A61C 9/006 433/29 |
| 2014/0365140 A1* | 12/2014 | Popilka | G06T 19/20 702/19 |
| 2015/0002649 A1* | 1/2015 | Nowak | A61B 5/1079 348/77 |
| 2015/0296184 A1* | 10/2015 | Lindenberg | A61C 9/0046 348/77 |

FOREIGN PATENT DOCUMENTS

| | | |
|---|---|---|
| DE | 10 2007 060263 A1 | 2/2009 |
| EP | 0 250 993 A2 | 1/1988 |
| EP | 2 166 303 A1 | 3/2010 |
| WO | 2009/063088 A2 | 5/2009 |
| WO | 2010/012838 A1 | 2/2010 |

\* cited by examiner

DEVICE FOR DETECTING THE THREE-DIMENSIONAL GEOMETRY OF OBJECTS AND METHOD FOR THE OPERATION THEREOF

BACKGROUND OF THE INVENTION

Field of the Invention

The invention relates to a device for detecting the three-dimensional geometry of objects, especially teeth, with a handpiece that has an optical apparatus with at least one camera and with at least one light source.

The invention furthermore relates to a method for operating a device for detecting the three-dimensional geometry of objects, especially teeth, with a handpiece that has at least one position sensor for detecting the change of the spatial position of the handpiece and an optical apparatus with at least one camera for taking pictures and with at least one light source for a projector.

Description Of The Related Art

A device of the initially-mentioned type is known from, for example, AT 508 563 B. In this case, the area of application of the invention extends to the recording of digital tooth and jaw impressions, assistance in diagnosis, supervision of tooth treatments, and reliable monitoring of inserted implants. In addition to further applications in the field of medical and industrial technology, for example in the field of endoscopy, objects that are poorly accessible can also be stereometrically measured.

The use of a position sensor is known from, for example, U.S. Pat. No. 5,661,519 A.

SUMMARY OF THE INVENTION

The object of the invention is to improve these devices such that they can be operated with a power supply that is as small as possible. Thus, operation by means of an energy storage mechanism that is housed in the handpiece itself and that is therefore small will be made possible.

In a device of the initially-mentioned type, this object is achieved in that the optical apparatus has exclusively rigidly attached parts and in that there is a means for producing light of the light source in the handpiece.

This object is achieved in a method of the initially-mentioned type in that it is determined—by the position sensor in the handpiece—how high a change in the spatial position of the device is, and from that it is determined how many pictures are taken by the camera within a defined unit of time.

By placing the means for generating light directly in the handpiece, long optical paths, for example over fiber optic cables or many deflection mirrors, are avoided. In this case, a differentiation is made between the light source, therefore everything that can emit light, for example the end of a fiber optic cable, and the means for producing light, for example a laser or the semiconductor of an LED.

By abandoning long optical paths, a means for producing light with lower output can be used in order to sufficiently illuminate the object. This means a notable energy savings.

The rigid mounting of all elements of the optical apparatus means that it is not possible to focus the optics of the camera. All calibrations of the optical apparatus therefore take place in the preliminary area. Here, it is especially important to achieve an optimum setting of the aperture. In this case, a smaller aperture is good for a larger depth of field; for a larger aperture, less illumination is required for a relatively good picture.

In one especially preferred embodiment, the device has an apparatus for synchronizing the power supply of the light source and the camera. Thus, the camera and light source are synchronously operated according to one preferred embodiment of the method. Large outputs with a comparatively small energy expenditure can be achieved by pulsing of light at spots. In this embodiment of the invention, the power supply is also interrupted on the sides of the picture. Thus, unilluminated pictures are avoided, and additional energy is saved.

In a further preferred embodiment, the handpiece has at least one position sensor, especially an acceleration sensor, a magnetic field sensor and/or a tilt sensor. With the latter, it is determined according to the method how large the change in the spatial position of the device is, and it is ascertained therefrom how many pictures are to be taken by the camera within one defined unit of time. In this way, taking more images of the same site with less motion than is necessary for optimum detection of the geometry can be avoided.

In this sense, in one preferred implementation, the image rate of images taken can be changed; preferably, the image rate is between 1 and 30 images per second.

In addition or alternatively, according to one preferred implementation of the method, the image rate can also be adapted depending on whether a higher or lower charging state of an energy storage mechanism or a higher or lower possible discharge current is available. Thus, for a higher charging state or discharge current, more light pulses can be emitted and received than at a lower charging state or discharge current.

In one possible embodiment of the invention, it can be additionally determined how many images of a defined region have been taken. From this value, a quality can be assigned to a recorded region of the object and can optionally be reproduced in the 3D display of the geometry of the object so that the user can react to it. Regions from which only a few data have been acquired and that therefore have a greater risk of deviations from the geometry of the object can be displayed in red, for example. Regions in which the number of pictures is already at a value that is sufficient for the desired quality can be displayed in green, for example. Other colors for the intermediate stages are likewise conceivable as for regions in which an optimum value has already been achieved; therefore, further pictures no longer entail a significant improvement of the acquired data. Of course, only regions that have poorer quality can also be colored.

For the purpose of saving energy, according to an additional or alternative process step for a defined region, it can be determined how many pictures of this region have already been taken and, upon reaching a defined number of pictures, no further pictures of this region are taken. This measure is, moreover, suitable for optimizing the required processing steps in a computer unit that processes the recorded data or for saving computing power that is required.

In one preferred embodiment, the optical apparatus has at least one projector for projection of patterns. The projection of patterns improves the possibilities for detecting the three-dimensional geometry.

In another preferred embodiment, the field angle of the camera and the field angle of the projector overlap one another at least 50%, preferably at least 80%, and especially preferably at least 90%. The field angle is the conical region in which the projection or picture-taking occurs. A proportion of the expended energy that is as large as possible is used due to the overlapping that is as large as possible.

In one preferred embodiment, the device has an electrical energy storage mechanism that can optionally be recharged.

The latter can be used as the sole energy source of the device. In this case, it is useful if the device furthermore has a data storage mechanism or a possibility of wireless data transmission. Thus, the device can be moved completely freely without a cable. In one embodiment in which the data are stored, it is appropriate to link the later transmission of data, for example via a USB connection, to the charging of the energy storage mechanism.

There is preferably an opening that can be hygienically or tightly sealed in the housing for replacement of the energy storage mechanism. Thus, for example, an operator after use of the scanner can replace the at least partially exhausted energy storage mechanism by a fully charged one. Alternatively or additionally, a skilled worker can also replace the energy storage mechanism after a certain number of charging cycles and an actual or expected decline of the output of the energy storage mechanism.

Alternatively or additionally, in a further preferred implementation of the invention, it can be ascertained from the determined value of the available charge whether the device is to be operated optionally with two or three or more cameras. Thus, different operating modes are formed for different outputs of the power supply or for different charging states.

In one especially preferred implementation of the method, the data that have been acquired by the camera are relayed to a computer unit or a storage medium without further processing or conditioning. Thus, the energy expenditure that otherwise for a processor or chip that conventionally carries out this processing or conditioning is completely avoided. The further processing in the computer unit can take place at least in part in the GPU; however, it has been shown that it is useful especially with respect to the speed of data processing to process in the GPU a part of the data acquired for detection or computation of the three-dimensional geometry. Thus, it is possible to convert the data, especially two-dimensional images that have been taken by means of the camera, without noteworthy loss of time, directly into a three-dimensional representation on a display or into a data file that is available on a storage medium (for example, a 3D file in STL format).

The device can have a thermovoltaic element according to one preferred embodiment. With this element, according to one preferred embodiment of the method, electrical energy can be obtained from the heat that arises during operation. This energy can be used, on the one hand, directly for operating the device; on the other hand, however, especially when the device is cooled, an energy storage mechanism can also be supplied with the energy obtained.

BRIEF DESCRIPTION OF THE DRAWING FIGURES

The invention is further explained below with reference to the drawings.

DETAILED DESCRIPTION OF THE INVENTION

Figure 1:
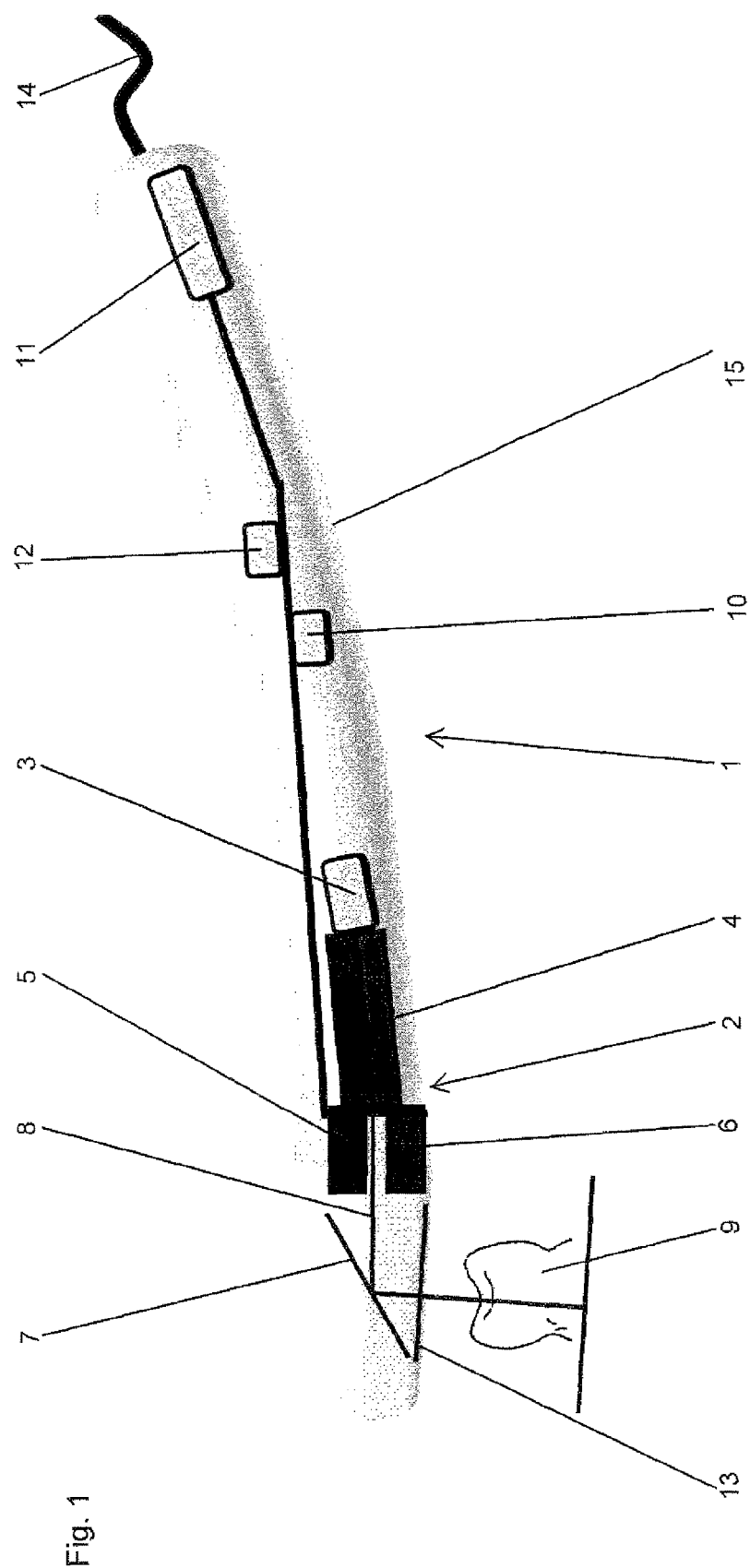
FIG. 1 shows a schematic representation of one embodiment of the invention.

FIG. 1 shows one exemplary embodiment of the device, consisting of a handpiece 1, in which there is an optical apparatus 2 that contains a light source 3, a projector 4, a first camera 5, a second camera 6, and a mirror 7. In front of the mirror in the housing 15 of the handpiece 1, there is a recess. The latter is provided with a transparent cover 13 for hygienic reasons and for protection of the components that are located in the handpiece 1.

In this embodiment, the light source 3 is an LED. In this embodiment, therefore, a means for producing the light (not shown in the drawings) is located in the form of a semiconductor directly in the light source 3. The further path of the light inside and outside of the device is shown by an exemplary light beam 8.

In this case, this beam first travels through the projector 4. Here, the projector 4 is used for projection of patterns onto the object. In this case, depending on the type of detection of the geometry, it can be both regular patterns, such as, for example, stripes, and irregular patterns, such as, for example, irregular point patterns.

Downstream from the projector 4, the light beam 8 is incident on the mirror 7 and is deflected via the mirror onto the object 9, whose geometry is to be detected. In the depicted embodiment, the object 9 is a tooth. In an embodiment that is not shown in the drawings and in which the light source 3 and the projector 4 are already aligned in the direction of the object, the mirror 7 can also be omitted.

The cameras 5, 6 record the pattern that has been projected onto the tooth 9 and from which later the geometry of the tooth 9 is computed. According to one preferred implementation, all computations in this respect take place in a computer unit that is located outside the handpiece 1, as a result of which the power consumption of internal chip sets or processors is minimized. The device can be connected to this computer unit both physically using a cable 14 and also wirelessly. In the embodiment, there is a wireless connection (for example, Bluetooth or WLAN). For this purpose, in the handpiece there is a means for wireless data transmission 10, especially a transmitter and optionally a receiver. The depicted cable 14 is therefore not connected during actual operation, but at a low charging state of the energy storage mechanism can be connected, for example, as auxiliary current.

Furthermore, in the handpiece 1, there is an energy storage mechanism 11 that can be optionally recharged. Consequently, a cable on the handpiece 1 can be completely omitted, as a result of which there is optimum freedom of motion.

The drawings, moreover, show a position sensor 12. With the latter, it can be determined how large the spatial motion of the handpiece 1 is. For this purpose, the position sensor 12 can be, for example, an acceleration sensor, a terrestrial magnetic field sensor or a tilt sensor. In this case, combinations of different sensor types increase the accuracy with which the change in the spatial position or the movement of the handpiece 1 is determined.

Figure 2:
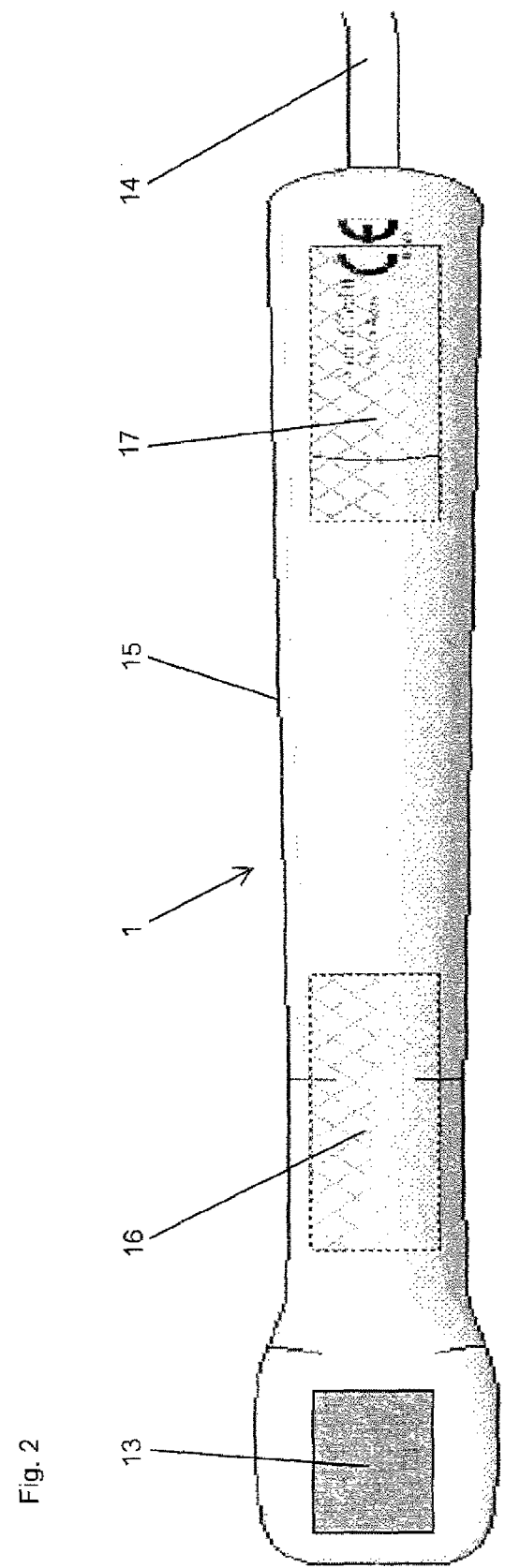
FIG. 2 shows a schematic view of the bottom of one embodiment of the invention.

FIG. 2 shows a schematic view of the bottom of one embodiment of the invention. Here, two regions 16, 17 are shown in which a thermovoltaic element could be placed.

In the first region 16, the thermovoltaic element is located directly on the bottom, therefore the side on which the covering 13 is located, in the vicinity of the optical apparatus 2. This is advantageous since the optical apparatus 2, especially the projector 4, produces mostly heat during operation and the heat can be used with losses that are as low as possible.

If the thermovoltaic element is placed in the second region 17, this has the advantage that it can be dimensioned to be larger; however, a heat conductor that conducts the heat from the optical apparatus 2 to the thermovoltaic element is then necessary. Also, in a positioning of the thermovoltaic element in the second region 17, attachment to the bottom of the handpiece 1 is useful, so that one side of the thermovoltaic element that releases heat and that points to the outside according to one preferred embodiment of the invention is not covered by the hand of the user.

The invention claimed is:

1. A hand-held device for detecting the three-dimensional geometry of objects, comprising:
    a handpiece that has an optical apparatus with at least one camera and at least one pulsed light source in the handpiece which projects a beam of light aligned with the at least one camera;
    a rechargeable power supply within the handpiece;
    a wireless transmitter within the handpiece; and
    an apparatus for synchronizing a power supply of the light source and the camera, wherein
    the optical apparatus has exclusively rigidly attached parts, and
    there is no cable to the hand-held device, whereby freedom of motion is optimized.

2. The device according to claim 1, wherein the optical apparatus has at least one projector for projection of patterns.

3. The device according to claim 2, wherein a field angle of the camera and a field angle of the at least one projector overlap one another at least 50%.

4. The device according to claim 2, wherein a field angle of the camera and a field angle of the at least one projector overlap one another at least 80%.

5. The device according to claim 2, wherein a field angle of the camera and a field angle of the at least one projector overlap one another at least 90%.

6. The device according to claim 1, wherein there is a transparent cover in a recess in a housing of the handpiece that covers the optical apparatus.

7. The device according to claim 1, wherein the handpiece has at least one position sensor, an acceleration sensor, a magnetic field sensor and/or a tilt sensor.

8. The device according to claim 1, wherein the rechargeable power supply is the sole power source of the device.

9. The device according to claim 1, wherein the device has a thermovoltaic element.

10. The device according to claim 9, wherein one side of the thermovoltaic element that absorbs heat is facing an interior of the handpiece, and wherein one side of the thermovoltaic element that releases heat is facing an exterior of the handpiece.

11. The device according to claim 9, wherein the heat-releasing side of the thermovoltaic element is connected to the housing of the handpiece in a thermally conductive manner.

12. The device according to claim 9, wherein the thermovoltaic element is connected to a power supply of the handpiece and/or to the energy storage mechanism.

13. The device according to claim 9, wherein one side of the thermovoltaic element that absorbs heat is facing an interior of the handpiece, towards electrical internals in the handpiece, and wherein one side of the thermovoltaic element that releases heat is facing an exterior of the handpiece.

14. The device according to claim 1, wherein the objects are teeth.

15. A device for detecting the three-dimensional geometry of teeth, comprising:
    a handpiece;
    two cameras in the handpiece;
    a pulsed light source in the handpiece projecting a beam of light between the two cameras, the two cameras and the pulsed light source being synchronously operated from a power source;
    at least one projector in the handpiece;
    a wireless transmitter within the handpiece; and
    a mirror in the handpiece, the mirror being configured to project the pulsed light through a covering to form a light pattern on the teeth, the mirror, the at least one projector, and pulsed light source and the two cameras forming an optical device;
    a rechargeable energy storage mechanism in the handpiece;
    a position sensor in the handpiece; and
    a thermovoltaic element in the handpiece, the thermovoltaic element being positioned either at a first region where the thermovoltaic element absorbs heat directly from the optical device, or at a second region where the thermovoltaic device absorbs heat from the optical device via a heat conductor, wherein
    all parts of the device are rigidly attached, and
    there is no cable to the hand-held device, whereby freedom of motion is optimized.

* * * * *